United States Patent
Dooris et al.

(10) Patent No.: US 7,101,398 B2
(45) Date of Patent: Sep. 5, 2006

(54) PROSTHETIC FACET JOINT LIGAMENT

(75) Inventors: Andrew Dooris, Fall River, MA (US); Hassan A. Serhan, S. Easton, MA (US); Mark Gracia, Rochester, MA (US)

(73) Assignee: Depuy Acromed, Inc., Raynham, MA (US)

( * ) Notice: Subject to any disclaimer, the term of this patent is extended or adjusted under 35 U.S.C. 154(b) by 81 days.

(21) Appl. No.: 10/334,601

(22) Filed: Dec. 31, 2002

(65) Prior Publication Data

US 2004/0127989 A1  Jul. 1, 2004

(51) Int. Cl.
*A61F 2/08* (2006.01)
*A61B 17/08* (2006.01)

(52) U.S. Cl. .............. 623/13.11; 623/14.13; 606/151

(58) Field of Classification Search .... 623/13.11–13.2, 623/14.13; 606/151
See application file for complete search history.

(56) References Cited

U.S. PATENT DOCUMENTS

| | | | |
|---|---|---|---|
| 4,255,820 A * | 3/1981 | Rothermel et al. ...... | 623/13.11 |
| 4,455,690 A | 6/1984 | Homsy | |
| 5,026,398 A * | 6/1991 | May et al. ............ | 623/13.11 |
| 5,263,984 A | 11/1993 | Li et al. | |
| 5,571,191 A | 11/1996 | Fitz | |
| 5,628,756 A | 5/1997 | Barker, Jr. et al. | |
| RE36,758 E | 6/2000 | Fitz | |
| 6,132,464 A | 10/2000 | Martin | |
| 6,280,444 B1 | 8/2001 | Zucherman et al. | |
| 6,342,060 B1 * | 1/2002 | Adams ................. | 606/151 |
| 6,419,703 B1 | 7/2002 | Fallin et al. | |
| 6,752,831 B1 * | 6/2004 | Sybert et al. ........... | 623/13.17 |
| 6,840,962 B1 * | 1/2005 | Vacanti et al. .......... | 623/23.76 |
| 2002/0065557 A1 | 5/2002 | Goble et al. | |
| 2002/0072800 A1 | 6/2002 | Goble et al. | |

FOREIGN PATENT DOCUMENTS

| | | |
|---|---|---|
| DE | 20112 123 U | 9/2001 |
| WO | WO 00/53126 A | 9/2000 |
| WO | WO 00/53126 A1 | 9/2000 |
| WO | WO 02/34120 A2 | 5/2002 |
| WO | WO 02/065954 A | 8/2002 |
| WO | WO 02/067793 A | 9/2002 |

OTHER PUBLICATIONS

Gardner, Alan and Pande, Ketan, C., Graf ligamentoplasty: a 7-year follow-up; Eur Spine J(2002) 11 (Suppl.2):S157-S163.
Senegas, J.; Mechanical supplementation by non-rigid fixation in degenerative intervertebral lumbar segments: the Wallis system; Eur Spine J(2002) 11 (Suppl.2):S164-S169.
European Search Report dated Oct. 5, 2004 EP03 25 8243.
Pending Non-published Patent Application Filed May 20, 2004 entitled Functional Spinal Unit Prosthetic, Inventors: Serhan et al.

* cited by examiner

*Primary Examiner*—David J. Isabella
(74) *Attorney, Agent, or Firm*—Thomas M. DiMauro

(57) ABSTRACT

This invention relates to a spinal facet joint ligament.

5 Claims, 13 Drawing Sheets

PROSTHETIC FACET JOINT LIGAMENT

BACKGROUND OF THE INVENTION

One of the most common surgical interventions today is arthrodesis, or spine fusion, in which two or more adjacent vertebral bodies are fused together in order to alleviate pain associated with the disc(s) located between those vertebral bodies. Approximately 300,000 such procedures are performed annually in the United States alone. Clinical success varies considerably, depending upon technique and indications, and consideration must be given to the concomitant risks and complications.

While spine fusion generally helps to eliminate certain types of pain, it has also been shown to decrease function by limiting the range of motion for patients in flexion, extension, rotation and lateral bending. Furthermore, it is believed that spine fusion creates increased stresses on (and, therefore, accelerated degeneration of) adjacent non-fused motion segments. Additionally, pseudoarthrosis, resulting from an incomplete or ineffective fusion, may reduce or even totally eliminate the desired pain relief for the patient. Also, the fusion device(s) used to effect fusion, whether artificial or biological, may migrate out of the fusion site, thereby creating significant new problems for the patient. Lastly, the recuperation time after a fusion procedure can be lengthy.

Recently, several attempts have been made to recreate the natural biomechanics of the spine through the use of an artificial disc. Artificial discs are intended to restore articulation between vertebral bodies so as to recreate the full range of motion normally allowed by the elastic properties of the natural disc, which directly connects two opposed vertebral bodies. However, the artificial discs developed to date do not adequately address the mechanics of motion of the spinal column.

In addition to the foregoing, posterior elements called the facet joints help to support axial, torsional and shear loads that act on the spinal column. Furthermore, the facet joints are diarthroidal joints that provide both sliding articulation and load transmission features. The facet's articular surfaces contact in extension, limiting rotation and increasing compressive load. The articular surfaces also contact on one side of the spine in lateral bending and axial rotation, also limiting rotation and transferring load.

However, the facet joints can also be a significant source of spinal disorders and, in many cases, debilitating pain. The articular cartilaginous surfaces can degenerate due to mechanical or biological factors and cause pain as with other joint osteoarthritis. For example, a patient may suffer from arthritic facet joints, severe facet joint tropism or otherwise deformed facet joints, facet joint injuries, etc. There is currently a lack of suitable intervention procedures for facet joint disorders. Facetectomy, or the removal of the facet joints, may provide some relief, but is also believed to significantly decrease the stiffness of the spinal column (i.e., hypermobility) in all planes of motion: flexion and extension, lateral bending, and rotation. Furthermore, problems with the facet joints can also complicate treatments associated with other portions of the spine. By way of example, contraindications for artificial discs include arthritic facet joints, absent facet joints, severe facet joint tropism or otherwise deformed facet joints. Accordingly, there is a need for a facet joint replacement that addresses these concerns.

U.S. Pat. No. Re. 36,758 (Fitz I) discloses an artificial facet joint where the inferior facet, the mating superior facet, or both, are simply covered with a cap. Because placement of the cap requires no preparation of the bone or articular surfaces; it covers and, therefore, preserves the bony and articular structures.

However, simple capping of the facet has several potential disadvantages. If the facet joint is osteoarthritic, a cap will not remove the source of the pain. Additionally, at least in the case of surface replacements for osteoarthritic femoral heads, the capping of articular bone ends has proven to lead to clinical failure due to mechanical loosening. This clinical failure is hypothesized to be a consequence of disrupting the periosteum and ligamentum teres femoris, both of which play a role in delivering nutrition to the femoral head, thereby leading to avascular necrosis of the bony support structure for the surface replacement. It is possible that corresponding problems could develop from capping the facet. Another potential disadvantage of facet capping is that in order to accommodate the wide variability in anatomical morphology of the facets, not only between individuals but also between levels within the spinal column, as well as due to associated hypertrophic and degenerative changes, a very wide range of cap sizes and shapes is required.

U.S. Pat. No. 6,280,444 ("Zuchermann") describes a spacer that is wedged between the spinous processes, a spinal extension stop, and methods to implant it. According to Zuchermann, the spacer limits rotation in extension (?) while providing flexion mobility. The U.S. Pat. No. 6,280,444 described a method to reduce stenosis by increasing posterior disc height and limiting extension. However, it is unknown exactly what function such a device would have. This device may abnormally loads the spinous processes and therefore could lead to abnormal bone remodeling. It affects the posterior elements and provides mobility, but does not alleviate posterior structures or address facet syndromes.

U.S. Pat. No. 6,132,464 ("Martin") describes a replacement of the articular surfaces and means for supporting and fixing these replacements to the posterior processes. The articulating surface itself is described as having "the shape, position, and orientation of a natural articular facet". It discloses a spinal facet joint prosthesis that is supported on the lamina (which is sometimes also referred to as the posterior arch). Extending from this support structure are inferior and/or superior blades that replace the cartilage at the facet joint. The prosthesis of U.S. Pat. No. 6,132,464 generally preserves existing bony structures and therefore does not address pathologies which affect the bone of the facets in addition to affecting the associated cartilage. Furthermore, the prosthesis of U.S. Pat. No. 6,132,464 requires a secure mating between the prosthesis and the lamina. However, the lamina is a very complex and highly variable anatomical surface. As a result, in practice, it is very difficult to design a prosthesis that provides reproducible positioning against the lamina so as to correctly locate the cartilage-replacing blades for the facet joints.

The U.S. Pat. No. 6,132,464 describes articular surfaces and means of attachment, but does not describe a capsular replacement.

U.S. Pat. No. 5,571,191 ("Fitz II") describes a facet prosthesis comprising superior and inferior components, pyramidal or conical in shape, fitting over the facet processes, and having low friction mating surfaces. Although this patent describes articular surfaces and means of attachment, it does not describe a capsular replacement.

Gardner et al. *Eur. Spine J* (2002) (Supp 2): S157–163, discloses Graf ligamentoplasty as a means of stabilizing and reducing mobility of one or more severely symptomatic motion segments associated with degenerative disc disease. FIG. 1 shows Polyester bands wrapped around a pair of pedicle screws extending from adjacent vertebral bodies. According to Gardner, appropriate Graf bands immobilizes the motion segment in lordosis with the facet joints in a position of full extension, in which position they are very stable. See page S159. Accordingly, Graf ligamentoplasty essentially immobilizes the facet joint. Gardner does not disclose a ligament that traverses a facet joint.

Senegas et al., *Eur. Spine J.* (2002) 11 (Supp 2): S164–9 discloses a Wallis implant system comprising a titanium interspinous blocker and a Dacron ligament, wherein the blocker is placed between two spinous processes and the Dacron ligament wraps around spinous processes. See p. S165. Accordingly, Senegas does not disclose a ligament that traverses a facet joint.

WIPO PCT Published patent application No. WO 00/53126 ("Ogun") discloses a memory metal implant for fixing an articulated joint, including a facet joint.

The Dynasis system is generally used as a replacement for the natural posterior longitudinal ligament. The system includes a cable housed inside a plastic sheath, and is attached to superior and inferior pedicles. The ligament of the Dynasis system does not traverse a facet joint.

SUMMARY OF THE INVENTION

The present inventors have appreciated that natural facet joints are true articulating joints in which the capsule surrounding the articular surfaces play a very important role. While the articular surface of the joint transfers compression, the capsule transfers tension. In flexion, the joint opens and the capsule is stretched. Several biomechanical in vitro studies have demonstrated the contribution of the capsule to total motion segment stiffness in flexion.

Replacing the articular surface may relieve pain, but does not fully restore joint functionality.

Accordingly, the present inventors recognized a need for stabilizing the facet joint in both compression and tension, and for preventing proliferation of debris from the implant site to the surrounding tissues.

In one aspect of the present invention, the facet joint is stabilized in both compression and tension by a prosthetic ligament having fasteners fixated either in the superior and inferior vertebrae or in superior and inferior prosthetic facet joint components. In some embodiments, the fasteners are selected from the group consisting of bone screws, hooks, wires, and pins. In some embodiments, the intermediate portion of the ligament is selected from the group consisting of a cable, a wires, an interconnected face, and a soft polymer bonded to the fastener and stretching between the superior and inferior fastener.

Accordingly, the present invention replaces the natural facet joint capsule with an. artificial construct that more fully provides the natural mechanical relationship provided by a natural healthy facet joint. In particular, by providing a ligament that stretches while resisting tension increases joint stability, the present invention more closely simulates physiological contributions of the facet joint capsule and so more closely approximates a full natural facet joint.

In one aspect of the present invention there is provided a prosthetic facet joint ligament. In preferred embodiments, this prosthetic facet joint ligament can be attached to anchoring points on opposing sides of a natural or prosthetic facet joint to provide a constraint against relative movement of the facet joints.

In a preferred embodiment of the present invention, the ligament is shaped as a sheath that can prevent debris produced by the facet articulation from spreading to the surrounding tissues, in particular to various neural structures. Previous facet joint replacement inventions describe resurfacing techniques that replace the contacting faces of the facet joint with metals or polymers. Due to unique variation in motions of the facet joint, these resurfaced contacting faces will inevitably produce wear debris, which is likely to irritate tissues. A membrane or sheath that surrounds the contacting faces and captures generated particles can reduce tissue irritation and inflammation. The membrane or sheath may also have structural integrity in itself and resist over-stretching and thereby supply resistance to tension.

In some embodiments, the prosthetic facet joint ligament is used in combination with other prosthetic facet joint components to produce a prosthetic facet joint having both load-bearing and movement-constraining functions.

Therefore, in accordance with the present invention, there is provided a prosthetic facet joint ligament.

In some embodiments, the prosthetic facet joint is used in combination with intervertebral body components to produce a total vertebral solution addressing both anterior and posterior loading and movement issues.

Therefore, in accordance with the present invention, there is provided a facet joint prosthesis for replacing a natural facet joint comprising first and second facets, the prosthesis comprising:
 a) a superior facet joint component having a superior outer surface adapted to attach to a superior facet,
 b) an inferior facet joint component having an inferior outer surface adapted to attach to an inferior facet, and
 c) a ligament adapted to constrain relative movement between the facets.

DETAILED DESCRIPTION OF THE INVENTION

Figure 1:
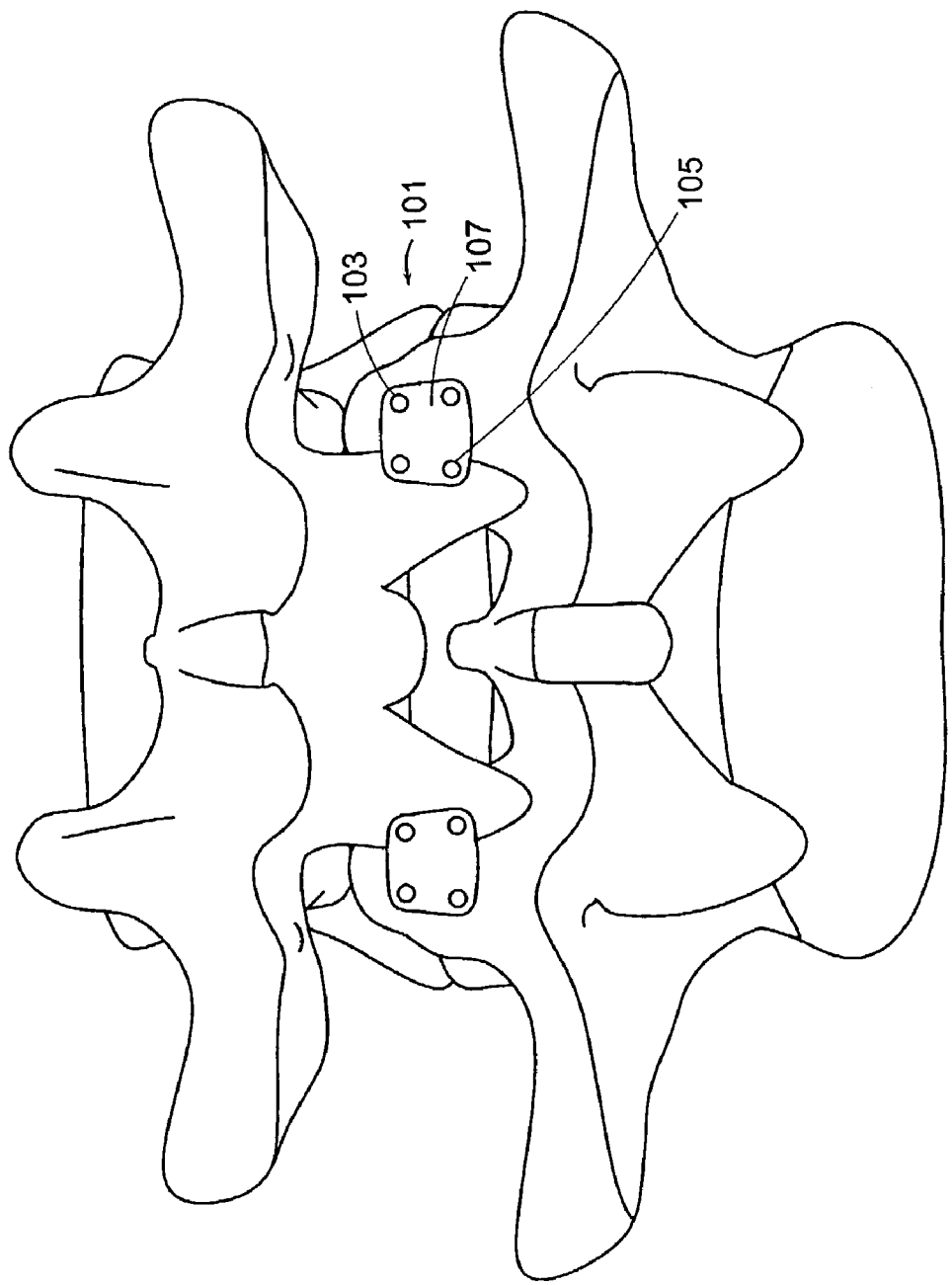
FIG. 1 discloses a pair of facet joint ligaments of the present invention attached across a pair of facet joints of a functional spinal unit.

Now referring to FIG. 1, there is provided a first embodiment of the facet joint ligament 101 of the present invention. The ligament comprises first 103 and second 105 attachment end portions and an intermediate portion 107. The first attachment end portions attaches to the superior facet SF of the facet joint, while the second attachment end portion attaches to the inferior facet IF of the facet joint. Thus, the ligament traverses the facet joint.

Figure 2:
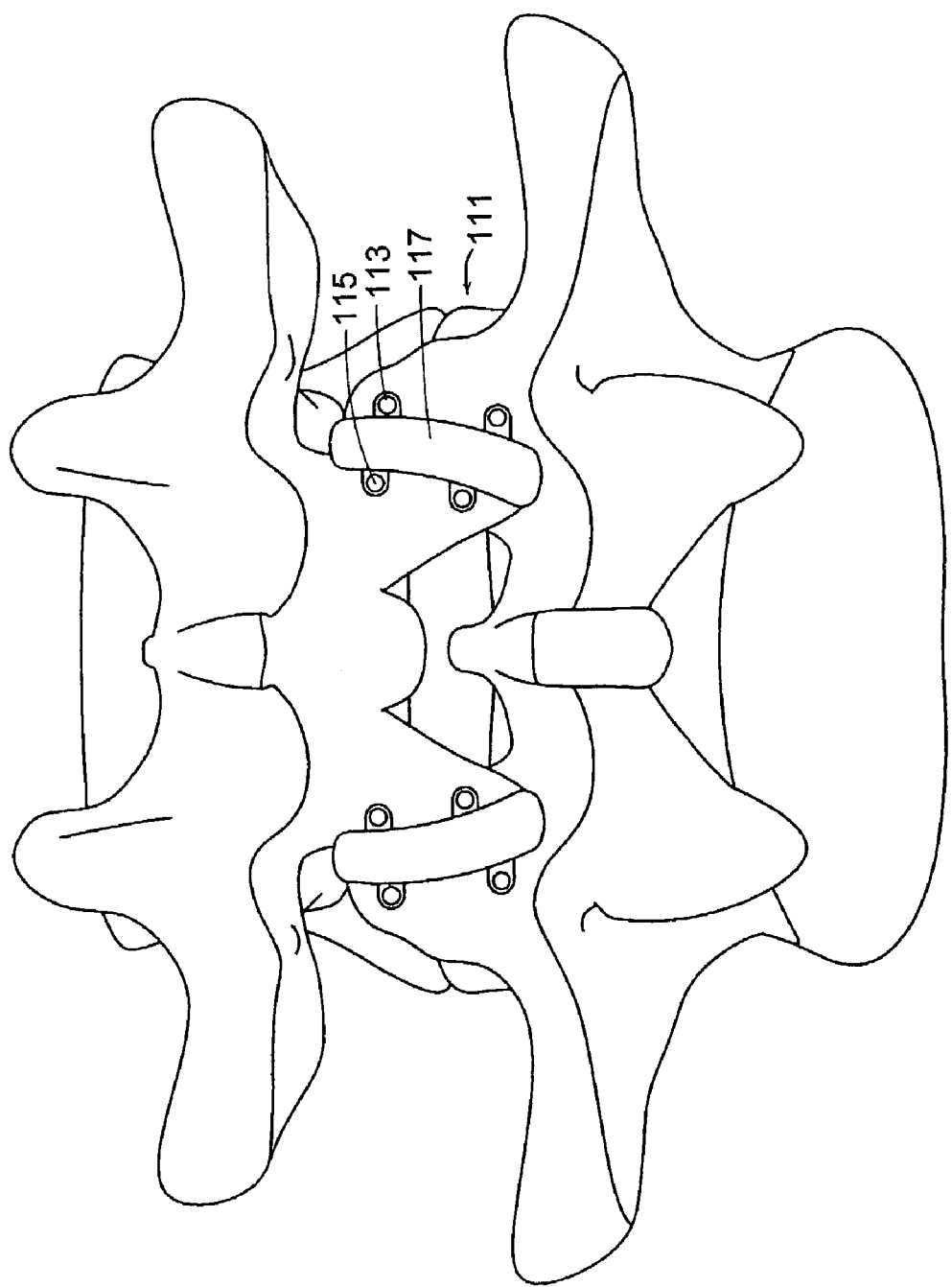
FIG. 2 discloses a pair of facet joint ligament of the present invention, wherein each ligament is a capsule, respectively, attached across a facet joint of the same functional spinal unit.

Now referring to FIG. 2, there is provided a second embodiment of the facet joint ligament of the present invention, wherein the ligament is a capsule 111 surrounding the facet joint The capsule comprises first 113 and second 115 attachment end portions and a sheath portion 117. The first attachment end portions attaches to the superior facet SF of the facet joint, while the second attachment end portion attaches to the inferior facet IF of the facet joint. The sheath traverses and completely circumscribes the facet joint. In this FIG. 2, the sheath may cover a portion of the exposed bony surface.

The ligament of the present invention can be made of any biocompatible material adapted for constraining but not totally eliminating relative movement between facet joints. In this regard, the facet joint ligament of the present invention mimics the natural facet joint capsule. The ligament of the present invention comprises three features. First it must be adapted to traverse a facet joint. Second, it must allow some flexion to occur across the facet joint. Third, it must resist excessive flexion of the facet joint.

In preferred embodiments, the ligament comprises a pair of attachment end portions and an intermediate portion.

Each attachment end portion of the ligament is adapted to attach to an anchoring surface on opposite sides of the facet joint. Typically, the attachment end portion comprises a fastener. In other cases, attachment may be provided by sutres or biologically compatible glues. However, in other embodiments, an attachment end portion can simply be terminus being identical in design to the intermediate portion. In such a case, the terminus is inserted into a port located on the anchoring surface, such as a port on a prosthetic having a facet joint articulating surface.

The intermediate portion of the ligament may be adapted to have desirable mechanical qualities found in ligaments, such as elasticity, flexibility, tensionability, and extensibility. Combinations of these qualities allows some displacement of the articular surfaces, but resists excessive displacement.

Preferably, the intermediate portion of the facet joint ligament is made from a nonbioresorbable material including polyesters, (particularly aromatic esters such as polyalkylene terephthalates, polyamides; polyalkenes; poly(vinyl fluoride); polyurethanes; polytetrafluoroethylene (PTFE); carbon fibres; silk; rubber, hydrogels, and glass, and mixtures thereof.

Preferably, the intermediate portion of the facet joint ligament is provided as a fabric. The fabric may be formed by a flat or circular weaving, knitting, braiding, crocheting or embroidery. Preferably, the fabric is braided in order to provide a high tensile strength. Preferred materials suitable for use as fabrics include polyester, polypropylene, polyethylene, carbon fiber, glass, glass fiber, polyurethane, polyaramide, metals, polymers, copolymers, polyactic acid (PLA), polyglycolic acid (PGA), silk, cellusoseic acid, and polycaprolactone fibers.

It is anticipated that, in use, the intermediate portion of the facet joint ligament may rub against soft tissue structures and damage not only those structures but itself as well. Therefore, in some embodiments, the intermediate portion of the facet joint ligament is lubricated. The lubricants lowers the friction coefficient between the ligament and the soft tissue, thereby lowering the wear. Preferred lubricants include hyaluronic acid, proteoglycans, and hydrogels In some embodiments, the ligament comprises a material having orthobiologic properties. This material will help the body's regenerative processes regrow a natural ligament to replace the prosthetic ligament of the present invention.

In some embodiments, the ligament comprises an orthoconductive portion. The orthoconductive portion typically has a porosity (preferably between about 20 µm and 250 µm) that is adapted to allow the ingress of the osteoconductive cells and an internal surface defined by the porosity that is adapted to attach these cells. In some embodiments, the orthoconductive portion comprises subintestinal submucosa (SIS).

In some embodiments, the ligament comprises an orthoinductive portion. The orthoinductive portion is preferably a protein, and is more preferably a growth factor. Preferred growth factors include factors from the TGF-beta and IGF-families.

In some embodiments, the ligament comprises an orthogenetic portion. The orthogenetic portion preferably comprises mesenchymal stem cells. More preferably, the MSCs are present in a concentration greater than that present in the patient's natural bone marrow.

In some embodiments, only the intermediate portion of the ligament comprises an orthobiologic material. In some embodiments, only the attachment end portion of the ligament comprises an orthobiologic material. In other embodiments, each of the intermediate and atachment end portions of the ligament comprises an orthobiologic material.

Preferably, the ligament is provided in a sterile form. In some embodiments, the ligment is sterilized, and then placed in a package. Preferably, the inside surface of the package is also sterile.

In some embodiments, the intermediate portion of the ligament is tensionable. A tensionable ligament sags when the ends of the ligaments are moved sufficiently closed to one another so that length of the ligament is less the distance between its ends. This quality allows the opposing facets to move closer to each other under loads without resistance from the ligament. A tensionable ligament also becomes taut when its ends are moved sufficiently away from one another so that length of the ligament is about equal to the distance between its ends. This quality constrains relative movement between the opposing facets.

In some embodiments, the tensibility of the ligament is between 10 and 50 N/mm.

In other embodiments, the ligament is not tensionable.

In some embodiments, at least a portion of the intermediate portion of the ligament is extensible. An extensible ligament has a first at-rest length when its ends are not loaded, and a second larger length when the ligament is subjected to tensioning. This quality allows the ligament to "give" a predetermined amount under tension. This quality is advantageous because the natural facet joint ligament is also extensible. Preferably, the ligament has an extensibility of between 45% and 65% of the at rest length of the ligament when subjected to a load of about 250 N.

In some embodiments, the extensibility of the ligament is between 30 and 70 N/mm.

In other embodiments, the ligament is not extensible.

In some embodiments, at least a portion of the intermediate portion of the ligament is flexible. A flexible ligament bows under axial loading/easily bends under physiologic flexural loading and easily regains its shape when the loading is ceased. This quality allows the ligament to "give" a predetermined amount while transferring stress under axial loading. This quality is advantageous because the natural facet joint ligament is also flexible. Preferably, the flexible portion of the ligament comprises a curved portion.

Now referring to FIGS. 5–8, there are provided some preferred embodiments of the ligament invention.

Figure 5:
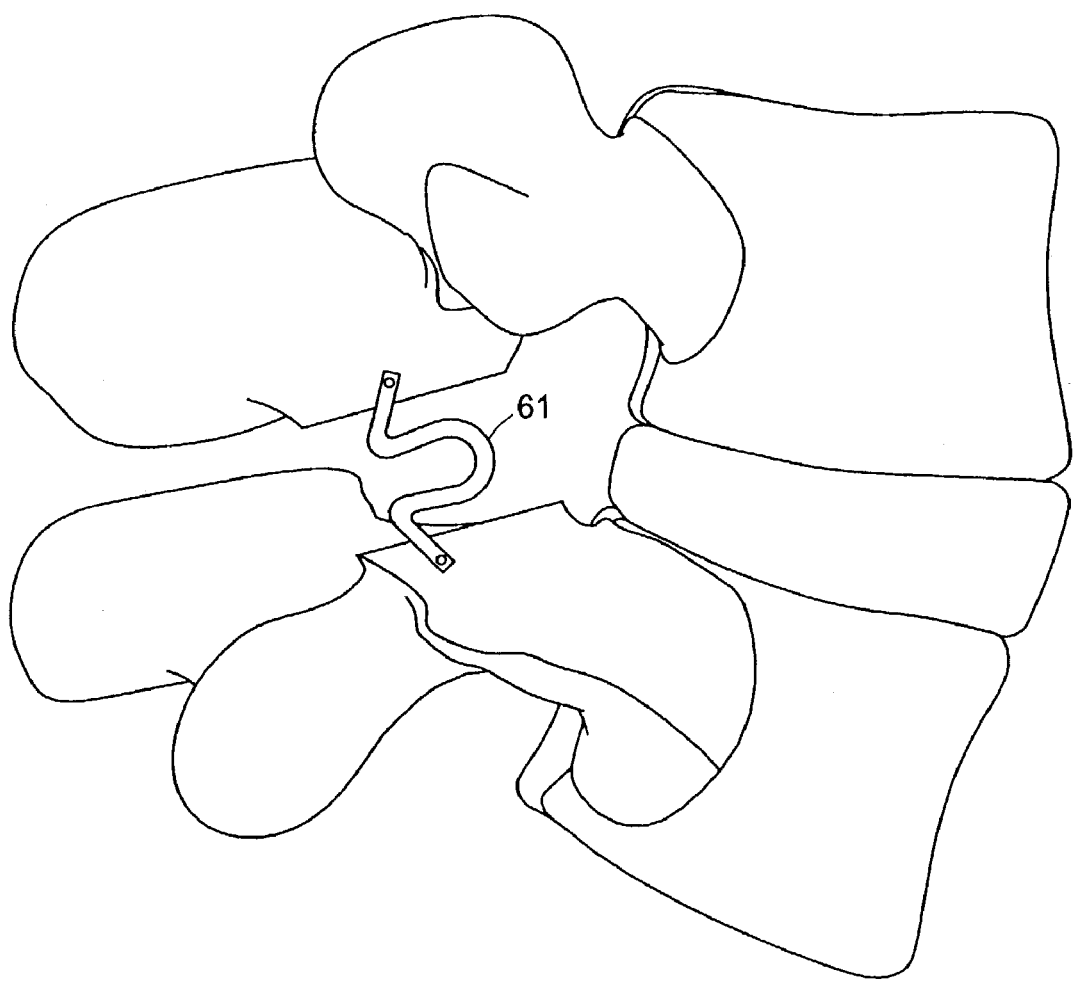
FIG. 5 discloses an embodiment of the ligament of the present invention comprising a curved, flexible intermediate portion attached across a facet joint.

Now referring to FIG. 5, in some embodiments, at least a portion of the ligament comprises a curved, flexible intermediate portion 61.

Figure 6:
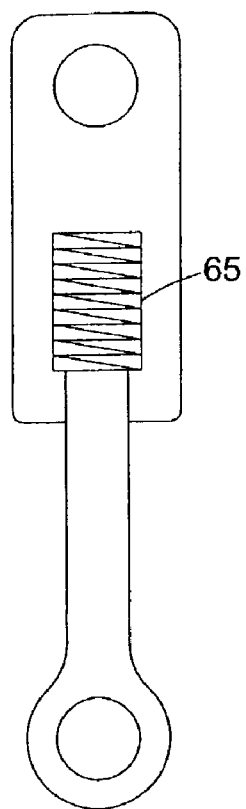
FIG. 6 discloses an embodiment of the ligament of the present invention comprising a spring intermediate portion.

Now referring to FIG. 6 in some embodiments, at least a portion of the ligament comprises a spring 65. The spring quality allows the ligament to initially yield to and eventually resist an axial compressive or tension load. In some embodiments, the spring is an expansion spring. In other embodiments, the spring is a compression spring.

In some embodiments, the intermediate portion of the ligament comprises a first 71 and second 73 intermediate portions bonded together. For example, now referring to FIG. 7, there is provided an embodiment of the ligament of the present invention comprising a pair of curved, flexible intermediate portions encapsulated in an encapsulant 75 (such as a polymer), wherein the ligament is adapted to attach across a facet joint. The advantage of this embodiment is its ability to provide elastic resistance to loads in a plurality of directions and its ability to resist substantial tensile forces due to interlocking members.

Figure 8:
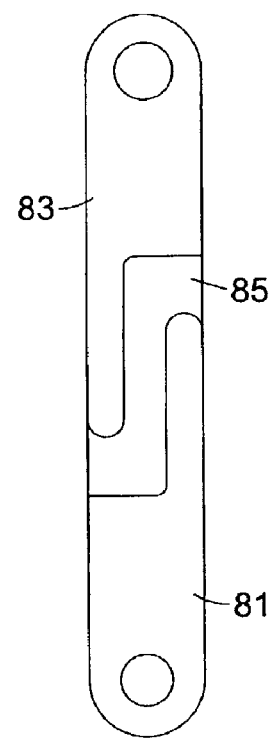
FIG. 8 discloses an embodiment of the ligament of the present invention comprising a a pair of straight intermediate portions attached by a polymer FIG. 9 discloses superior and inferior prosthetic facets having opposed articulating surfaces.
Figure 7:
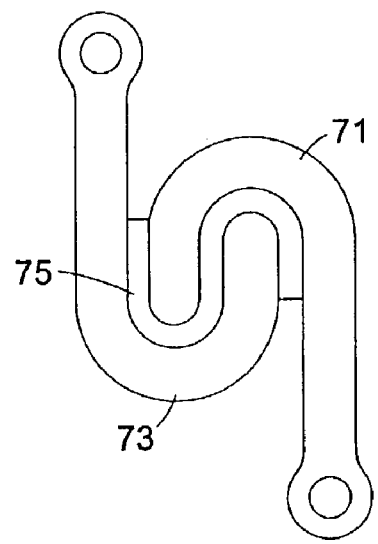
FIG. 7 discloses an embodiment of the ligament of the present invention comprising a a pair of curved, flexible intermediate portions encapsulated in a polymer.

Now referring to FIG. 8, there is provided an embodiment of the ligament of the present invention comprising a pair of straight intermediate portions 81,83 attached by a bonding material 85 (such as a polymer), wherein the ligament is attached across a facet joint. The advantage of this embodiment is its simple design and small size.

In embodiments to be used in the lumbar spine, the ligament of the present invention preferably has a length of between about 1 cm and about 4 cm. It preferably has a width of between about 0.5 cm and about 1 cm.

In some embodiments, the ligament comprises a sheath. In these embodiments, the width of the sheath is much greater. In preferred sheaths, the sheath is sized to substantially enclose the facet joint. In some embodiments, the sheath is fluid permeable. This feature permits the ingress of fluids that help lubricate the joint, while preventing the egress of wear debris from the facet joint articulation surfaces. In some embodiments, the sheath contains a lubricating fluid, thereby imitating a natural facet joint capsule. In preferred embodiments, the sheath may be pre-assembled prior to implantation, or it may be attached via glues, sutres, wires, thermally activated coagulation or in situ polymer embedding.

As noted above, in some embodiments, the attachment end portions of the facet joint ligament comprise a pair of fasteners. The function of the fastener is to join to attachment surfaces located on either side of the facet joint in order to securely fasten the intermediate portion of the facet joint ligament across the facet joint. The fastener may be adapted to fasten the facet joint ligament to attachment surfaces located upon either:

a) a facet joint prosthetic component, or b) a bony surface located adjacent the facet joint prosthetic component.

The attachment end portions of the prosthetic ligament of the present invention may be attached to any two anchoring surfaces on opposite sides of the facet joint, provided the ligament traverses the facet joint . These anchoring surfaces may be located on a bony surface of the opposing vertebrae, or on other prosthetic facet joint components.

In one embodiment, the first attachment end portion of the ligament is adapted to attach to a first load-bearing portion of a facet joint prosthesis. This embodiment is surgeon friendly in that the attachment can be made by the manufacturer prior to surgery, thereby providing ease of use and repeatability.

Figure 15:
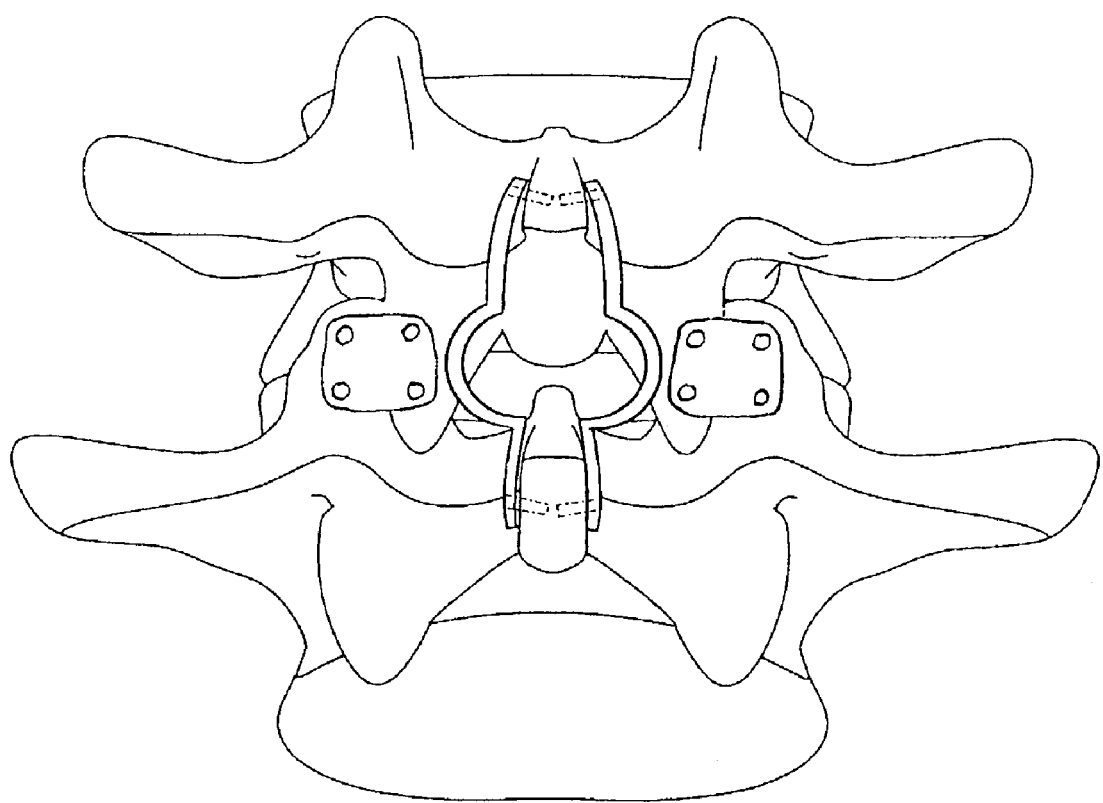
FIG. 15 discloses an embodiment of the ligament of the present invention attached across a pair of spinous processes coupled with a prosthetic facet joint.

In another embodiment, first attachment end portion of the ligament is adapted to attach to a portion of the natural vertebra. In some embodiments thereof, the vertebral body is used as the anchoring surface. In another, the facet portion of the vertebra is the anchoring surface. In other, and now referring to FIG. 15, the spinous process is used as an anchoring surface.

Figure 16:
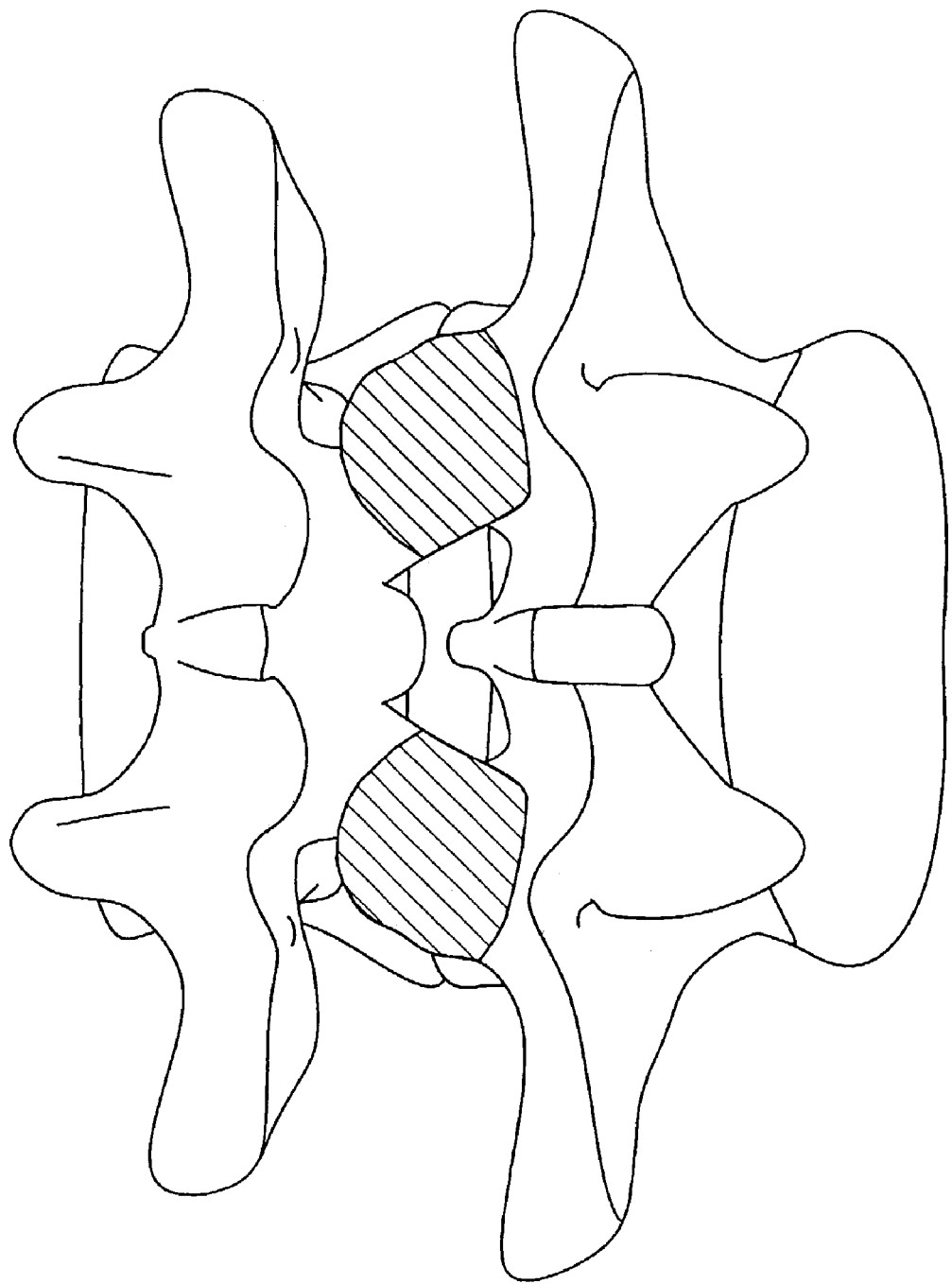
FIG. 16 discloses an embodiment of the ligament of the present invention wrapped around a facet joint.

In another embodiments, the first end portion of the ligament is adapted to attach to the transverse process. In another embodiments, the first end portion of the ligament is adapted to attach to the pedicle. In another embodiments, and now referring to FIG. 16, the ligament is wrapped around the facet joint.

The fastener may be any design known in the art, including winged, barbed or screw-in mechanisms. Preferably, the fastener is a barbed anchor, as it prevents pullout and is easily inserted. When the attachment surface is a bony surface, the fastener may be a bone fastener.

Preferably, the ligament and fastener components are pre-connected. That is, the components are physically attached prior to their placement upon the spine. Pre-connected components are advantageous because their secured attachment to each other are guaranteed, and the surgeon need not waste time in making the attachment. Components may be pre-connected by physical locking, physical connection (as in FIG. 3) by bonding, or by making the components from the same material and integrally connecting them. When the preconnected components are integrally formed (by, for example, molding or thermoforming), there is no danger of micromotion. Therefore, in accordance with the present invention, there is provided a facet joint ligament comprising:

a) a ligament comprising first and second end portions, and b) first and second fasteners, wherein the first fastener is pre-connected to the first end portion of the ligament, and the second fastener is pre-connected to the second end portion of the ligament.

Figure 3A:
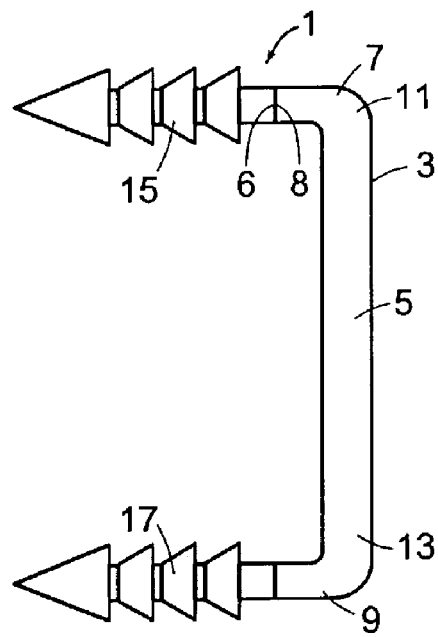
FIG. 3 discloses preferred embodiments of a facet joint ligament of the present invention.
Figure 3B:
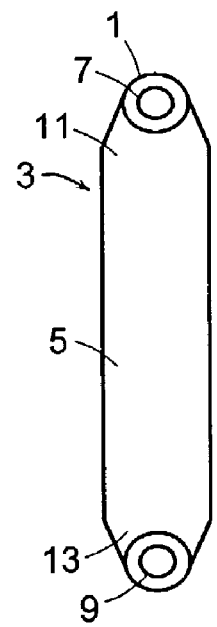

Now referring to FIGS. 3a and 3b, there is provided a facet joint ligament 3 having:
i) an intermediate portion 5,
ii) first and second end portions 7,9, and
iii) first and second conformable portions 11, 13, wherein the first conformable portion is disposed between the intermediate portion and the first end portion, and the second conformable portion is disposed between the intermediate portion and the second end portion, and
iv) first and second fasteners 15,17, wherein the first end portion 7 is shaped to cooperatively connect to the first fastener 15, and the second end portion 9 is shaped to cooperatively connect to the second fastener 17.

Figure 3C:
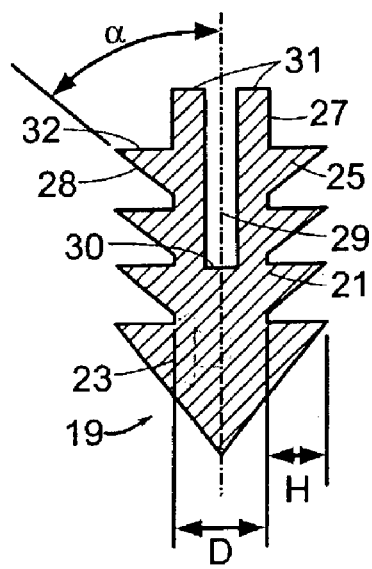
Figure 3D:
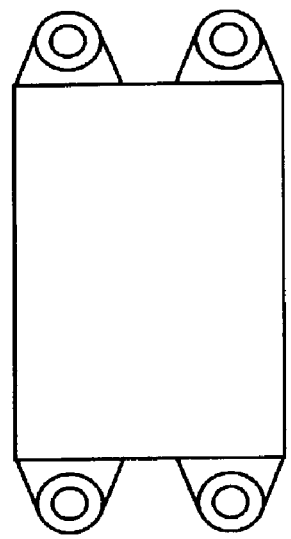

Now referring to FIG. 3c, preferably, the fastener 19 comprises a longitudinal shank 21, an insertion end 23 comprising protrusions 25 laterally extending from the shank, and an attachment end 27 having an upper surface 31 for connecting to the ligament.

Preferably, the lateral protrusions have leading edges 28 which define an angle α of no more than 45 degrees relative to the axis of the shank. In such embodiments, the bearing of the leading edge against the vertebral body surface will not substantially impede the progress of the bone fastener into the bone. Preferably, the leading edges define an angle of no more than 30 degrees, and more preferably between about 20 degrees and 30 degrees. When the angle α is between 20 and 30 degrees, the angle is sufficiently small to not impede the progress of the bone fastener, and yet sufficiently large to insure its secure fit.

In some embodiments, the height H of the protrusions on the bone fastener is no more than 70% of the diameter D of the longitudinal shank. When this condition is selected, the risk that any protrusion will act as a shoulder and stop further entry of the bone fastener into the vertebra is minimized. Preferably, the H/D ratio is no more than 40%, more preferably between about 20% and 40%. Within this more preferred window, the protrusion height is sufficiently small to not impede the progress of the bone fastener, and yet sufficiently large to insure its secure fit.

The outer diameter (2H+D) of the bone fastener is preferably between about 3–9 mm, more preferably about 4–6 mm. The length $L_{BF}$ of the bone fastener is preferably between about 3–45 mm, more preferably between about 15–25 mm.

In some embodiments, the attachment end of the bone fastener is made of a ceramic material. When the bone fastener is ceramic, it can withstand the high impact of the driver without failing. Therefore, in accordance with the present invention, there is provided an facet joint ligament comprising:
a) a compressible intermediate portion comprising first and second end portions, and
b) first and second fasteners, each fastener having an attachment end comprising a ceramic material and a shank comprising a polymer material.

In some embodiments, at least the end portions of the intermediate portion and the attachment end of the bone fastener are made of the same material. When the materials are so selected, these portions may be easily made and pre-connected in an integral fashion. This feature also eliminates the need for sutures.

Referring back to FIG. 3c, in another aspect of the present invention, the attachment end 27 of the fastener is configured to accept a driver element. When this configuration is selected, the bone fastener may be driven into the bone by simply providing axial force to the upper surface 31 of the fastener through the driver. Therefore, in accordance with the present invention, there is provided a facet joint ligament comprising:
a) a ligament comprising first and second end portions, and
b) first and second fasteners, wherein the first bone fastener is connected to the first end portion of the ligament, and the second bone fastener is connected to the second end portion of the ligament, and wherein the first bone fastener is configured to accept a driver.

Preferably, the configuration defines a recess 29 upon the upper surface 31 of the attachment end 27 of the fastener. This recess 29 is configured to accept the driver (not shown).

In some embodiments, the recess 29 of the bone fastener may be configured to allow insertion of a rescue screw, thereby allowing retrieval of the bone fastener.

Figure 4:
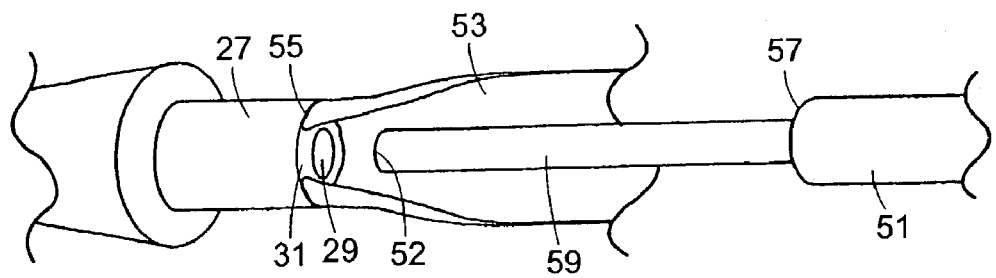
FIG. 4 discloses a driver used to attach the facet joint ligament of FIG. 3

Now referring to FIG. 4, in some embodiments, the system has a port for accepting a driver 51 which drives the bone fastener into the vertebral body. In FIG. 4, the port comprises a recess 29. In some embodiments, the end portion 53 of intermediate portion is molded to the upper surface 31 of the attachment end 27 of the fastener such that an insertion tip 59 of driver 51 can be inserted into the recess 29 without damaging the ligament. FIG. 4 illustrates such an attachment wherein the end portion 53 of the intermediate portion is attached semi-circumferentially to the outer edge 55 of the upper surface 31 of the fastener. It is appreciated that other embodiments may function similarly, such as attaching the intermediate portion of the ligament to one half face of the fastener upper surface 31 and modifying the driver shoulder to contact the other half face of the fastener surface. Furthermore, the lower surface 57 of the driver shoulder is able to contact the upper surface 31 of the bone fastener. Preferably, the lower surface 52 of the insertion tip 59 is also able to contact the bottom 30 of the fastener recess 29. With these features, the driver can be used to fully seat the fastener in the bony attachment surface and apply pretension to the ligament. When the diameter of recess 29 is substantially equal to the diameter of tip 59, the insertion tip will temporarily reinforce the fastener during the insertion step.

In some embodiments, the lower surface 30 of the recess is located at a depth such that both the distal end of tip 59 and shoulder 59 will respectively contact the lower surface 30 (as shown in FIG. 3c) and upper surface 31 of the recess.

In some embodiments, the ligament of the present invention is adapted to replace the natural interspinous or intertransverse ligament. In other embodiments, the ligament of the present invention is adapted to replace the facet joint capsule.

In many embodiments, the attachment end portions of the ligament of the present invention are attached to the anchoring surfaces on opposite sides of the facet joint in order to constrain the relative movement of the facets.

As noted above, the facet joints are diarthroidal joints that provide both sliding articulation and load transmission features. The facet's articular surfaces contact in extension, limiting rotation and increasing compressive load.

Preferably, the facet joint ligament of the present invention will be used in conjunction with other prosthetic components designed to mimic the load-bearing and preferably the sliding articulation functions of the natural facet joint. Therefore, in accordance with the present invention, now referring to FIGS. 9 and 10, there is provided a facet joint prosthesis for replacing a natural facet joint comprising first and second facets, the prosthesis comprising:

a) a superior facet joint component 91 having an outer surface 93 adapted to attach to a superior facet, b) an inferior facet joint component 95 having an outer surface 97 adapted to attach to an inferior facet, c) a facet joint ligament 99 adapted to constrain relative movement between the superior and inferior facets.

In some embodiments, the superior and inferior facet joint components disclosed in Fitz I, Fitz II, Zuchermann and Martin, supra, the specifications are which are incorporated by reference, are selected.

In embodiments of the present invention comprising a prosthesis having superior and inferior facet joint components, the outer surfaces thereof may comprise an attachment feature. Preferred attachment features are selected from the group consisting of teeth, keels, spikes, pins, and combinations thereof. In some embodiments, the outer surface is shaped to conform to the natural facet surface, that is, convex.

Figure 9:
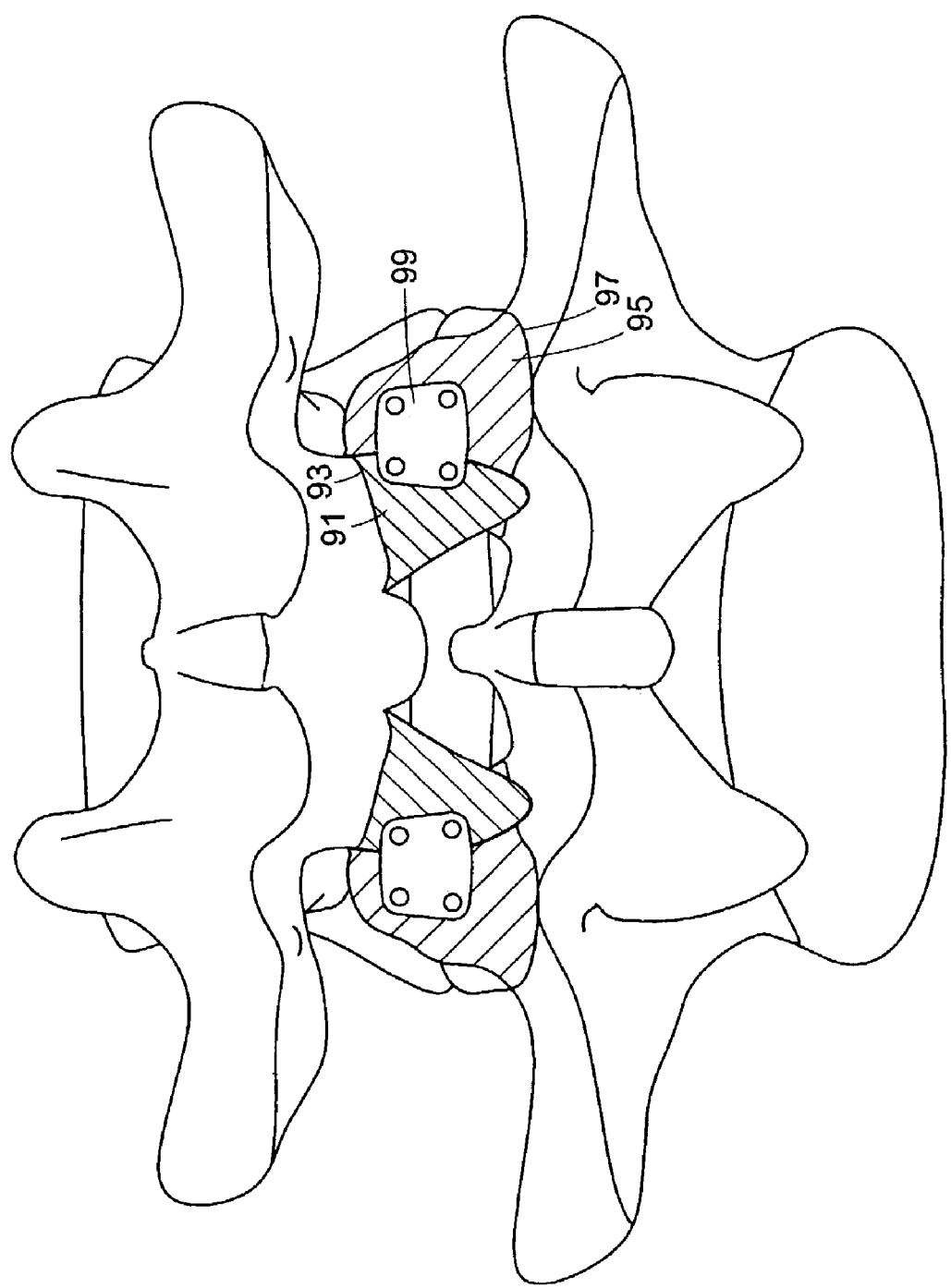

Now referring to FIG. 9, in some embodiments of the present invention, the superior and inferior facet joint components of the prosthesis are independent bodies. In preferred embodiments thereof, the superior facet joint component forms a superior endplate having an outer surface adapted to attach to a first facet and an inner articulation surface, while the inferior facet joint component forms an inferior endplate having an outer surface adapted to attach to an inferior facet and an inner articulation surface. In this embodiment, the inner articulation surfaces are adapted to form an articulation interface. For the purposes of the present invention, this embodiment is called an "articulation prosthesis".

In some articulation embodiments, the first inner articulation surface is convex shaped, while the second inner articulation surface is concave shaped. This creates a ball and socket joint well known in the art.

In some embodiments, the first and second articulation surfaces are conforming. In others, the first and second articulation surfaces are non-conforming.

Figure 10:
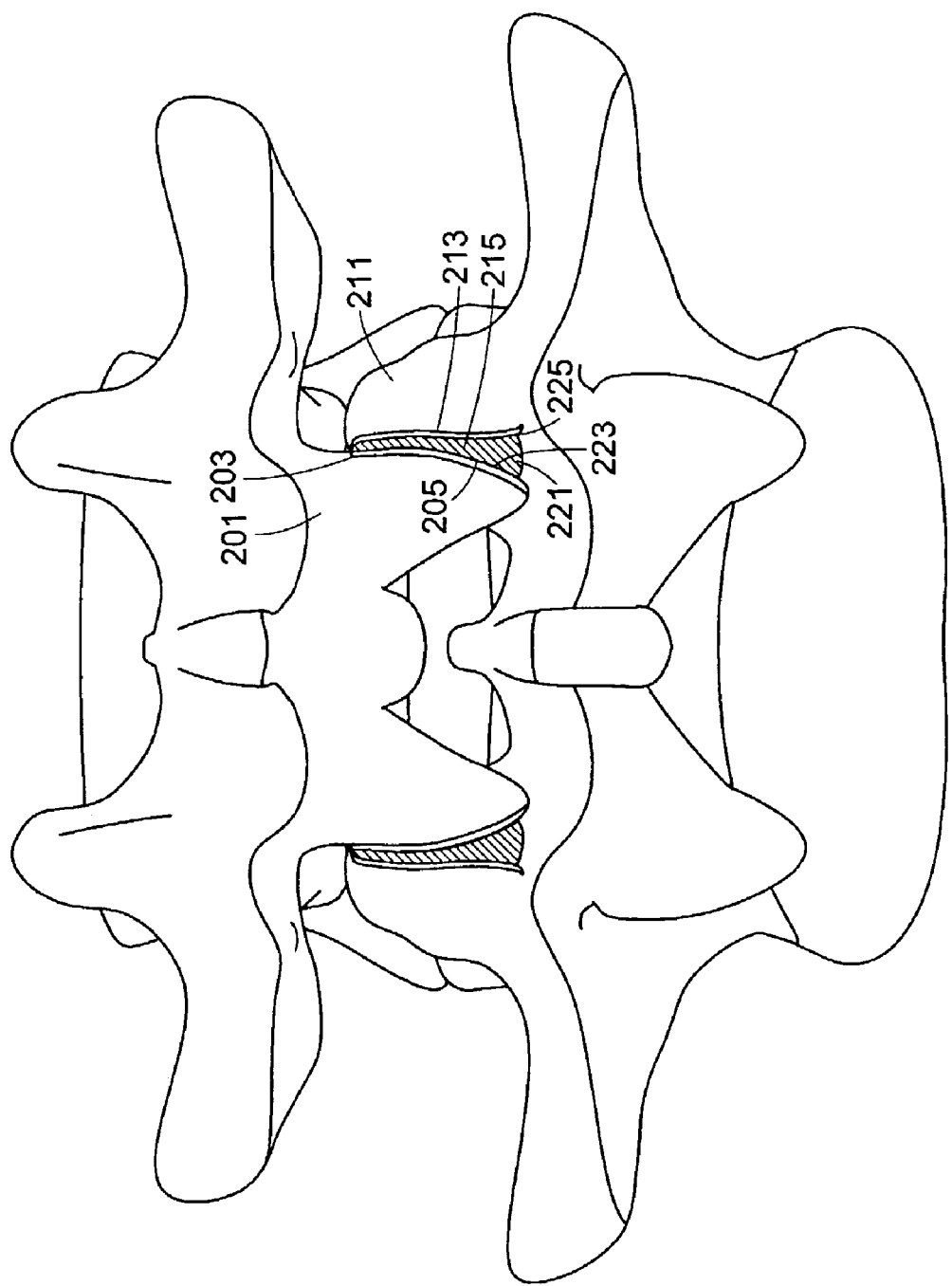
FIG. 10 discloses superior and inferior facets having a prosthetic cushion attached therebetween.

Now referring to FIG. 10, in other embodiments, the superior and inferior facet joint components do not have inner articulation surfaces, but rather are joined by an elastic cushion core. In preferred embodiments thereof, the "cushion-type" prosthesis comprises:

a) a superior facet joint component 201 forming a superior endplate having an outer surface 203 adapted to attach to a superior facet and an inner surface 205, b) an inferior facet joint component 211 forming an inferior endplate having an outer surface 213 adapted to attach to an inferior facet and an inner surface 215, c) an elastic core 221 having a superior surface 223 adapted to attach to the inner surface of the superior facet joint component and an inferior surface 225 adapted to attach to the inner surface of the inferior facet joint component.

For the purposes of the present invention, this embodiment is called a "cushion prosthesis". In preferred embodiments thereof, the device comprises an elastomer adapted to elastically compress during axial loading and relax when the load is lifted.

The superior and inferior facet joint components of the present invention may be made from any material appropriate for human surgical implantation, including but not limited to all surgically appropriate metals including titanium, titanium alloy, chrome alloys and stainless steel, and non-metallic materials such as carbon fiber materials, resins, plastics and ceramics.

The elastic core may comprise polyurethanes, foamed polyethylene, silicones, rubbers, copolymers or hydrogels. In other embodiments, the elastic core is formed of an orthobiologic material such as hyaluronate, collagen or subintestinal submucosa.

In some embodiments of the present invention having both a pair of prosthetic facet joint articulating surfaces and a prosthetic facet joint ligament, the invention limits the natural spinal extension. In these embodiments, extension is limited to no more than 7 degrees, preferably no more than 5 degrees. Preferably, the device stiffness is at least 2 Nm/degrees in order to so limit the extension.

In some embodiments of the present invention having both a pair of prosthetic facet joint articulating surfaces and a prosthetic facet joint ligament, the invention limits the axial compression of the prosthetic articulating surfaces. In these embodiments, axial compression is limited to between 0.1 mm and 2 mm, and is preferably between 0.5 and 1.5 mm. In this preferred range, the axial compression is similar to that of the natural healthy facet joint.

In some embodiments of the present invention having a prosthetic facet joint ligament, the invention resists flexion. In these embodiments, flexion is limited to no more than 15 degrees, and preferably is no more than 12 degrees. Preferably, the tensile strength of the prosthetic capsule is between 50 and 300 N, is preferably at least 100 N, and is more preferably at least 200 N.

In some embodiments of the present invention having both a pair of prosthetic facet joint articulating surfaces and a prosthetic facet joint ligament, the invention resists axial rotation. In these embodiments, a pair of devices of the present invention are preferably used so that each facet joint of a functional spine unit has a device, whereby a first device limits the axial rotation while the ligament of the second device is put in tension. This motion tends to produce coupled motion with flexion and bending. In some embodiments, the prosthetic articulating surfaces of the first device are sufficiently strong to withstand compressive forces of at least 100N, and more preferably at least 150N, and more preferably at least 200N.

In some embodiments of the present invention having both a pair of prosthetic facet joint articulating surfaces and a prosthetic facet joint ligament, the invention resists at least anterior-posterior shear. In these embodiments, the prosthetic articulating surfaces contact and the prosthetic articulating surfaces are sufficiently strong to withstand contact shear forces of at least 500N, and more preferably at least 750N, and more preferably at least 1000N.

In some preferred embodiments, at least one prosthetic facet joint component is used in conjunction with an anterior-based intervertebral body device. Preferably, the at least one prosthetic facet joint component is selected from the group consisting of the superior facet joint component, the inferior facet joint component, and the facet joint ligament, and combinations thereof.

Preferably, the intervertebral body device is selected from the group consisting of:

a) an interbody fusion device, and b) a motion device.

Preferred motion devices are selected from the group consisting of articulating devices, cushion devices, nucleus pulposus replacements and devices comprising a compound adapted to promote nucleus pulposus regeneration ("orthobiologic disc device").

Preferred interbody fusion devices are disclosed in U.S. Pat. No. 4,834,757 ("Brantigan"), and U.S. Pat. No. 5,489,308 ("Kuslich"), the specifications of which are incorporated by reference.

Figure 11:
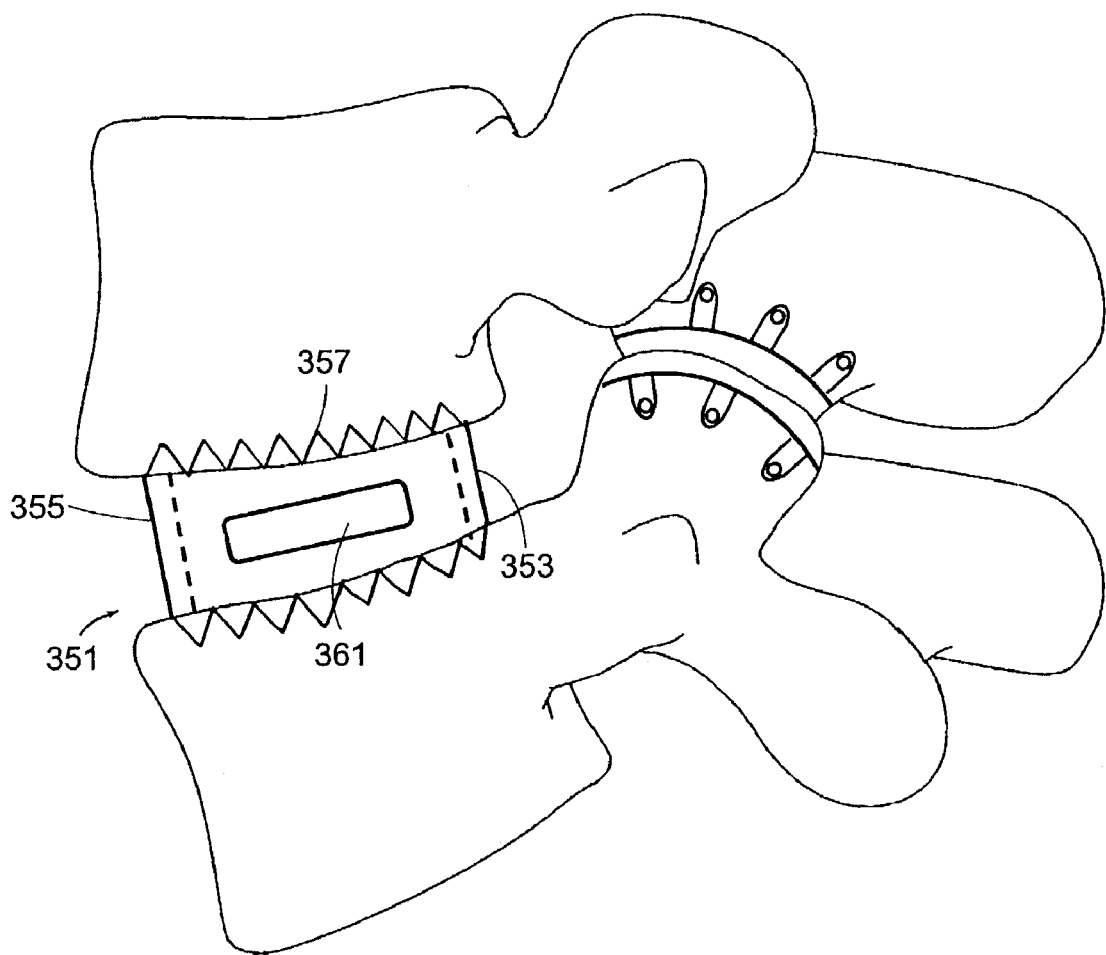
FIG. 11 discloses a pair of facet joint ligament of the present invention, wherein the ligament is a capsule, attached across a pair of facet joints of a functional spinal unit having a fusion cage inserted therein.

Now referring to FIG. 11, there is provided:

a) an artificial interbody spinal fusion implant 351 for insertion within an implantation space formed across the height of a disc space between vertebral bodies of a human spine, the vertebral bodies having an anterior aspect and a posterior aspect and a depth therebetween, said implant comprising;

a leading end 353 for insertion first into the disc space and a trailing end 355 opposite said leading end, said implant having a length from said leading end to said trailing end;

a top 357 and a bottom 359 between said leading and trailing ends adapted to space apart the adjacent vertebral bodies, said top and said bottom each preferably having at least one opening 361 therethrough, said openings being in communication with one another to permit for the growth of bone from adjacent vertebral body to adjacent vertebral body through said implant, said implant having a height H from said top to said bottom;

opposite sides between said top and said bottom, and between said leading and trailing ends, said implant having a width W from one of said sides to the other of said sides, the height of said implant preferably being less than the width of said implant;

said implant being formed at least in part of a material other than bone; and said implant being configured to be wholly contained within the perimeter of the adjacent vertebral bodies, and b) a facet joint ligament.

Preferred articulating motion devices are disclosed in U.S. Pat. Nos. 5,556,431 and 5,674,296, the specifications of which are incorporated by reference.

Figure 12:
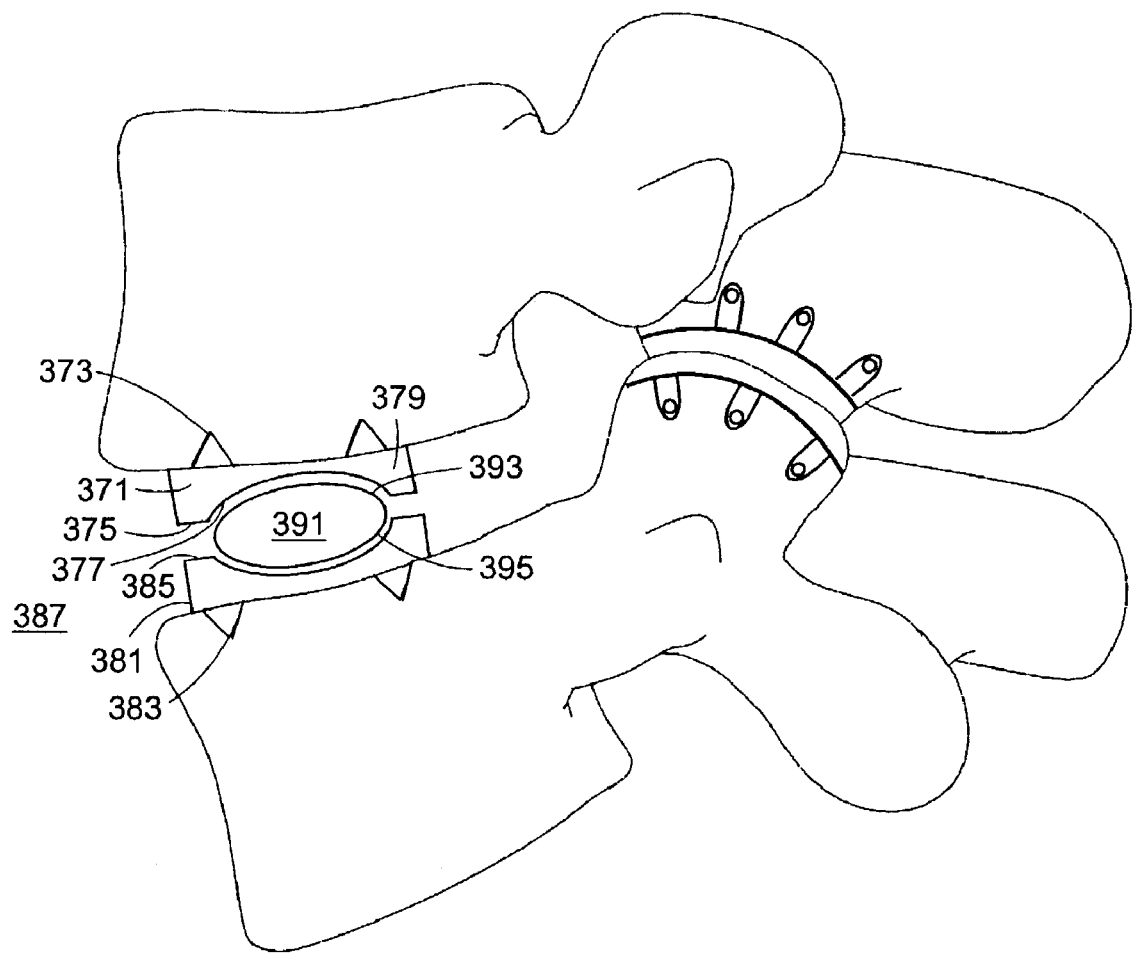
FIG. 12 discloses a pair of facet joint ligament of the present invention, wherein the ligament is a capsule, attached across a pair of facet joints of a functional spinal unit having a three-piece motion disc inserted therein.

Now referring to FIG. 12, in some embodiments, the articulating motion disc is a three piece design. Thus, the invention comprises:

a motion disc comprising:
 a) a first prosthetic vertebral endplate 371 comprising:
  i) an outer surface 373 adapted to mate with a first vertebral body,
  ii) an inner surface 375 having a first articulation surface 377,
  iii) a body portion 379 connecting the inner and outer surfaces,
 b) a second prosthetic vertebral endplate 381 comprising:
  i) an outer surface 383 adapted to mate with a second vertebral body, and
  ii) an inner surface 385 comprising a first articulation surface 387,
 c) a core member 391 comprising:
  i) a first articulation surface 393 adapted for articulation with the first articulation surface of the first endplate, and
  ii) a second articulation surface 395 adapted for articulation with the first articulation surface of the second endplate, wherein the core member is oriented to produce a first articulation interface between the first articulation surface of the first endplate and the first articulation surface of the core member, and a second articulation interface between the first articulation surface of the second endplate and the second articulation surface of the core member, and a facet joint ligament.

Figure 13:
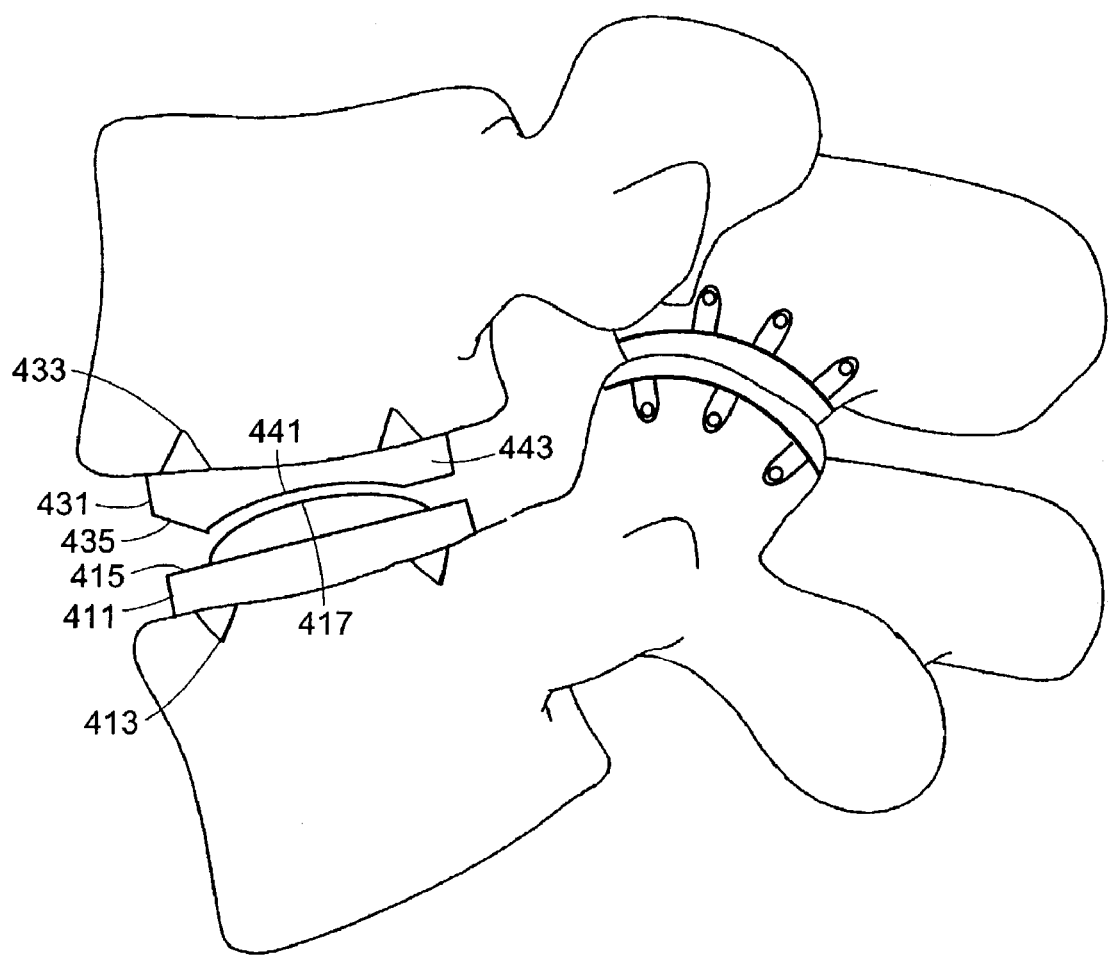
FIG. 13 discloses a pair of facet joint ligament of the present invention, wherein the ligament is a capsule, attached across a pair of facet joints of a functional spinal unit having a two-piece motion disc inserted therein.

Now referring to FIG. 13, in some embodiments, the articulating motion disc is a two piece design. Thus, the invention comprises:

a motion disc 401 comprising:
 a) a first prosthetic vertebral endplate 431 comprising:
  i) an outer surface 433 adapted to mate with a first vertebral body,
  ii) an inner surface 435 having a first articulation surface 441,
  iii) a body portion 443 connecting the inner and outer surfaces,
 b) a second prosthetic vertebral endplate 411 comprising:
  i) an outer surface 413 adapted to mate with a second vertebral body, and
  ii) an inner surface 415 comprising a second articulation surface 417, wherein the first and second articulation surfaces are oriented produce an articulation interface, and a facet joint ligament.

Other preferred articulating motion devices are disclosed in U.S. Pat. Nos. 6,368,350 and 5,507,816, the specifications of which are incorporated by reference.

Preferred cushion motion devices are disclosed in U.S. Pat. Nos. 6,136,031; 5,071,437; and 5,645,597, the specifications of which are incorporated by reference.

Figure 14:
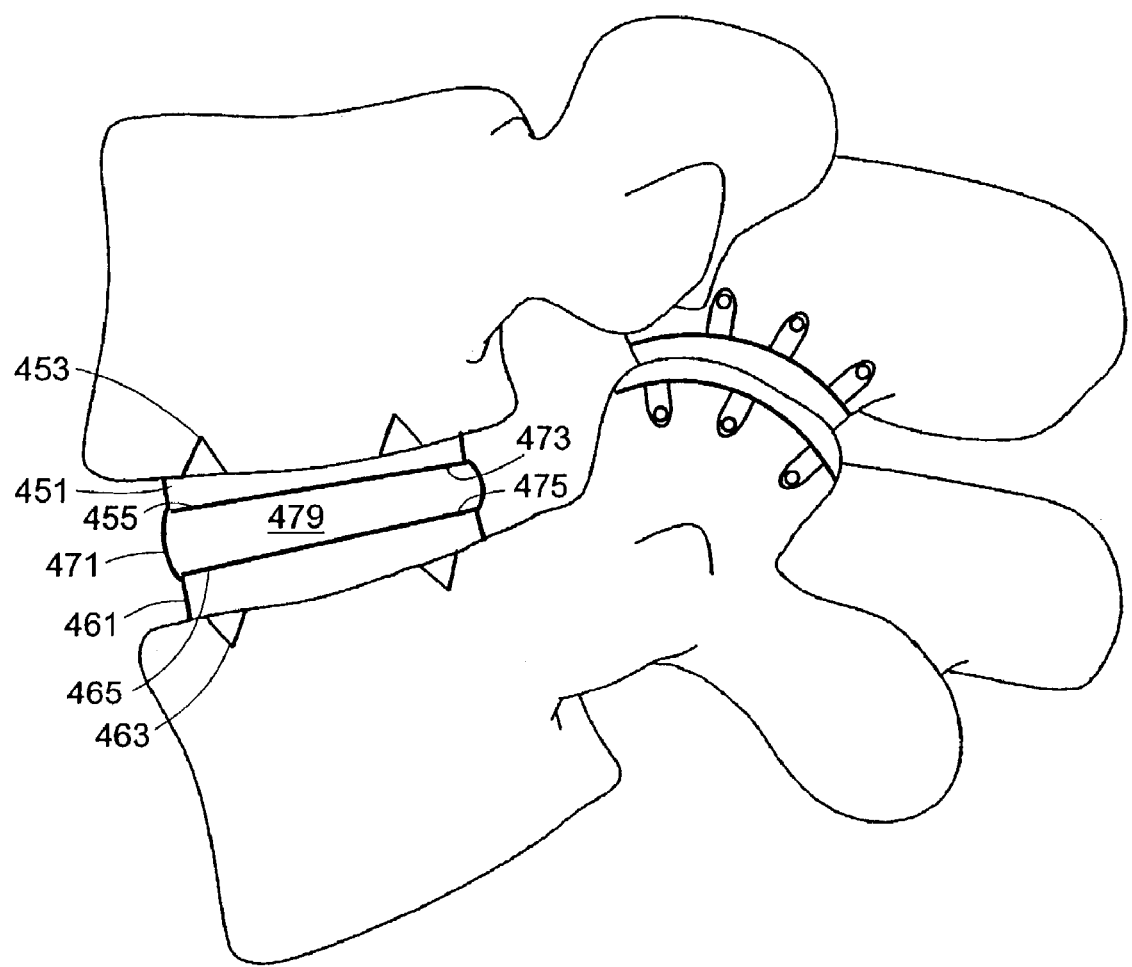
FIG. 14 discloses a pair of facet joint ligament of the present invention, wherein the ligament is a capsule, attached across a pair of facet joints of a functional spinal unit having a cushion-type motion disc inserted therein.

Now referring to FIG. 14, in some embodiments, the motion disc is a cushion disc and the invention comprises:

a cushion motion disc comprising:
 a) a first prosthetic vertebral endplate 451 comprising:
  i) an outer surface 453 adapted to mate with a first vertebral body,
  ii) an inner surface 455,
  iii) a body portion 453 connecting the inner and outer surfaces,
 b) a second prosthetic vertebral endplate 461 comprising:
  i) an outer surface 463 adapted to mate with a second vertebral body, and
  ii) an inner surface 465,
 c) a core cushion member 471 comprising:
  i) a first attachment surface 473 adapted for attachment to the first articulation surface of the first endplate, and
  ii) a second attachment surface 475 adapted for articulation with the first articulation surface of the second endplate, and
  iii) an elastic body portion 479 connecting the first and second attachment surfaces of the core cushion member.

Preferred nucleus pulposus replacement devices are disclosed in U.S. Pat. Nos. 5,976,186, 5674,295 and 6,264,695, the specifications of which are incorporated by reference.

We claim:

1. A prosthetic facet joint ligament for stabilizing a natural facet joint, comprising a pair of attachment end portions and an intermediate portion, wherein each attachment end portion of the ligament is adapted to attach to an anchoring surface on opposite sides of the natural facet joint, and wherein each attachment end portion comprises a fastener, and wherein the intermediate portion comprises first and second intermediate portions having curved ends, each comprising a nonbioresorbable material selected from the group consisting of polyesters, polyurethanes; polytetrafluoroethylene (PTFE); carbon fibres; silk; rubber, hydrogels, and glass, and mixtures thereof, wherein the curved ends of the first and second intermediate portions are interlocking members attached to each other by a bonding material.

2. The ligament of claim 1 wherein the intermediate portion comprises an elastic portion.

3. The ligament of claim 2 wherein the elastic portion comprises a polyester.

4. The ligament of claim 2 wherein the elastic portion comprises rubber.

5. The ligament of claim 1 wherein the intermediate portion is braided.

* * * * *